United States Patent [19]

Graham

[11] Patent Number: 5,127,537
[45] Date of Patent: Jul. 7, 1992

[54] TISSUE CASSETTE WITH A LIVING HINGE

[76] Inventor: Donald R. Graham, 664 Trotwood Ridge Rd., Pittsburgh, Pa. 15241

[21] Appl. No.: 710,587

[22] Filed: Jun. 5, 1991

[51] Int. Cl.⁵ ............................................. B65D 43/16
[52] U.S. Cl. ................................. 220/339; 220/306; 220/337
[58] Field of Search .............. 220/339, 337, 334, 307; 215/235, 237

[56] References Cited

U.S. PATENT DOCUMENTS

| Re. 28,165 | 9/1974 | McCormick | 425/117 |
|---|---|---|---|
| Re. 30,861 | 2/1982 | Krawagna | 16/293 |
| 3,674,396 | 7/1972 | McCormick | 425/117 |
| 3,741,447 | 6/1973 | Miles et al. | 222/517 |
| 4,034,884 | 7/1977 | White | 220/306 X |
| 4,141,312 | 2/1979 | Louder et al. | 118/7 |
| 4,220,252 | 9/1980 | Beall et al. | 220/307 |
| 4,346,810 | 8/1982 | Kneissl | 215/237 |
| 4,386,714 | 6/1983 | Roberto et al. | 220/339 |
| 4,414,705 | 11/1983 | Ostrowsky | 220/339 X |
| 4,421,246 | 12/1983 | Schultz et al. | 220/307 |
| 4,487,324 | 12/1984 | Ostrowsky | 215/235 |
| 4,545,495 | 10/1985 | Kinsley | 215/235 |
| 4,549,670 | 10/1985 | Trendler | 220/338 |
| 4,573,600 | 3/1986 | Dubach | 215/237 |
| 4,615,462 | 10/1986 | Sacherer et al. | 220/339 |
| 4,625,898 | 12/1986 | Hazard | 215/235 X |
| 4,638,916 | 1/1987 | Beck et al. | 215/235 |
| 4,778,071 | 10/1988 | Fillmore | 215/237 |
| 4,782,985 | 11/1988 | Kinsley | 222/481.5 |
| 4,793,502 | 12/1988 | Beck | 215/235 |
| 4,813,560 | 3/1989 | Begley | 215/235 |
| 4,832,219 | 5/1989 | Nycz | 215/235 |
| 4,848,612 | 7/1989 | Beck | 215/235 |
| 4,854,473 | 8/1989 | Dubach | 220/335 |
| 4,911,324 | 3/1990 | Dubach | 220/339 |
| 4,911,337 | 3/1990 | Rosenthal | 222/498 |
| 4,997,100 | 3/1991 | Dudek | 220/306 |

*Primary Examiner*—Stephen Marcus
*Assistant Examiner*—Vanessa Caretto
*Attorney, Agent, or Firm*—Webb, Burden, Ziesenheim & Webb

[57] ABSTRACT

A tissue cassette for holding biological tissue specimens. The tissue cassette includes an open topped, perforated base member adapted to receive a tissue specimen, a perforated lid member adapted to cover the base member and a snap action hinge joining the base member to the perforated lid. The snap action member can be J-shaped, sinusoidal shaped or L-shaped. Further, the cassette can include a living hinge for joining the base member to the open topped base member. The living hinge includes a first end attached to the lid member, a second end attached to the base member, a flat first surface and a curved second surface, whereby the hinge thickness varies across the length of the hinge and the thinnest portion of the hinge is positioned between the hinge ends. The curved surface can be concave shaped and the hinge can have a constant width from the first end to an intermediate section and decreasing width from the intermediate section to the second end. The intermediate section on the hinge second end is offset to permit the breaking away of the hinges flush with the base member surface.

19 Claims, 6 Drawing Sheets

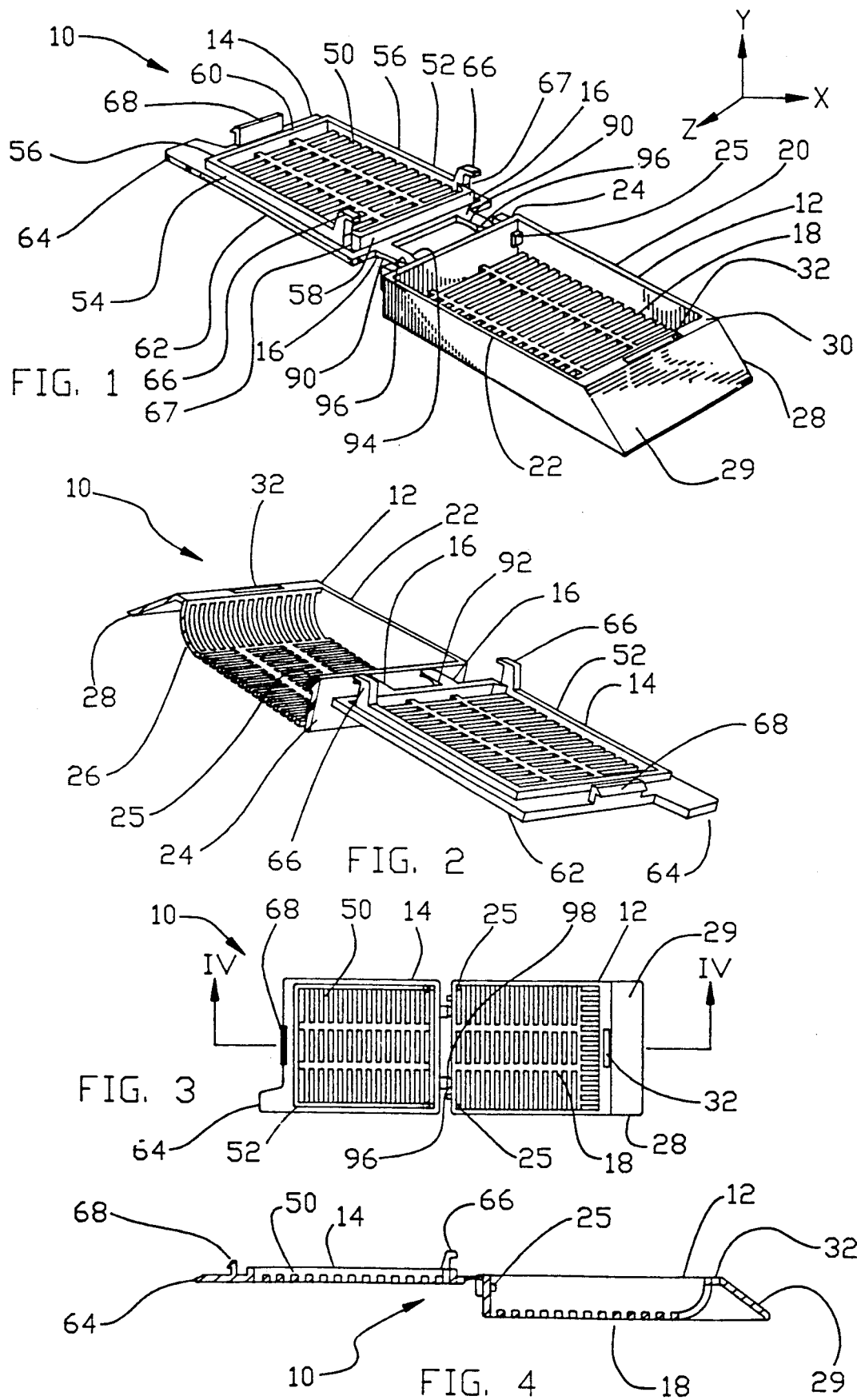

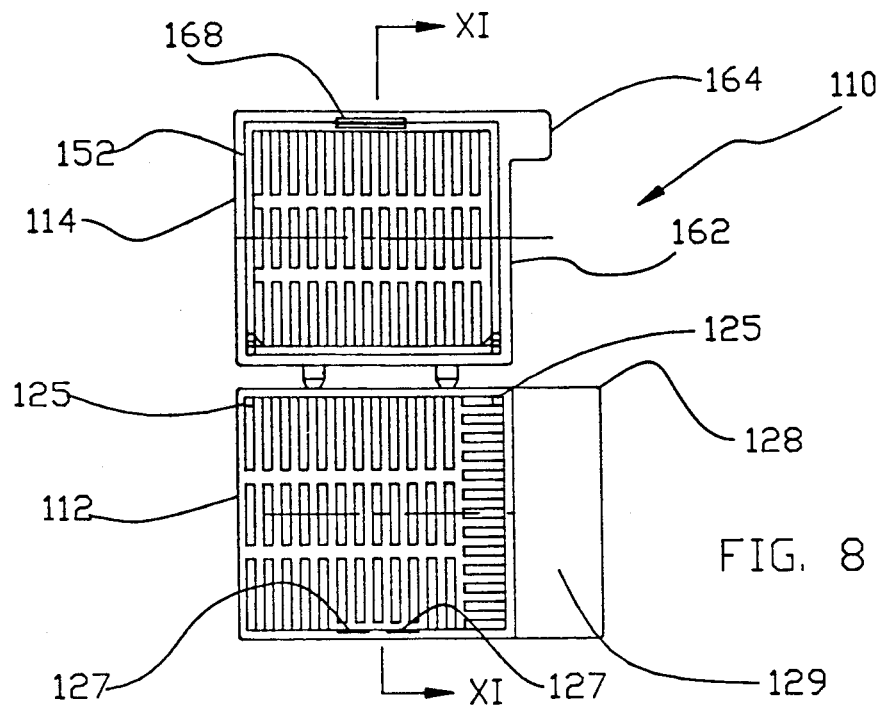
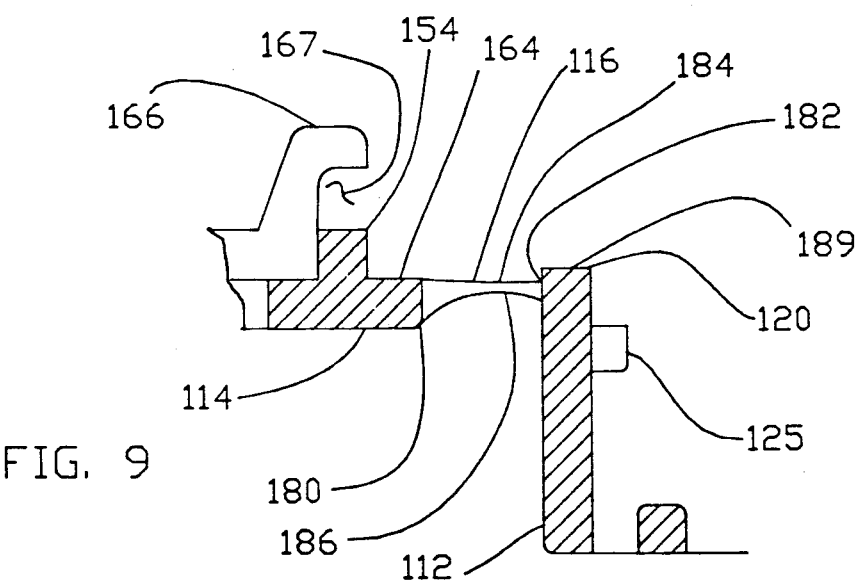
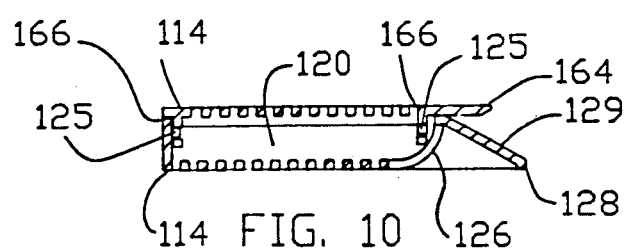
FIG. 10
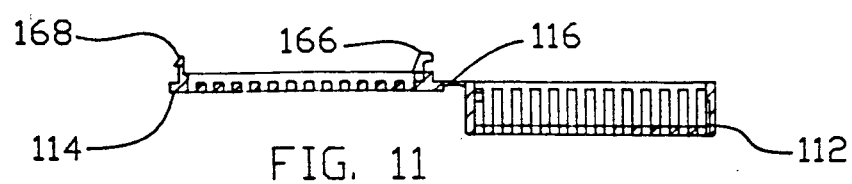
FIG. 11

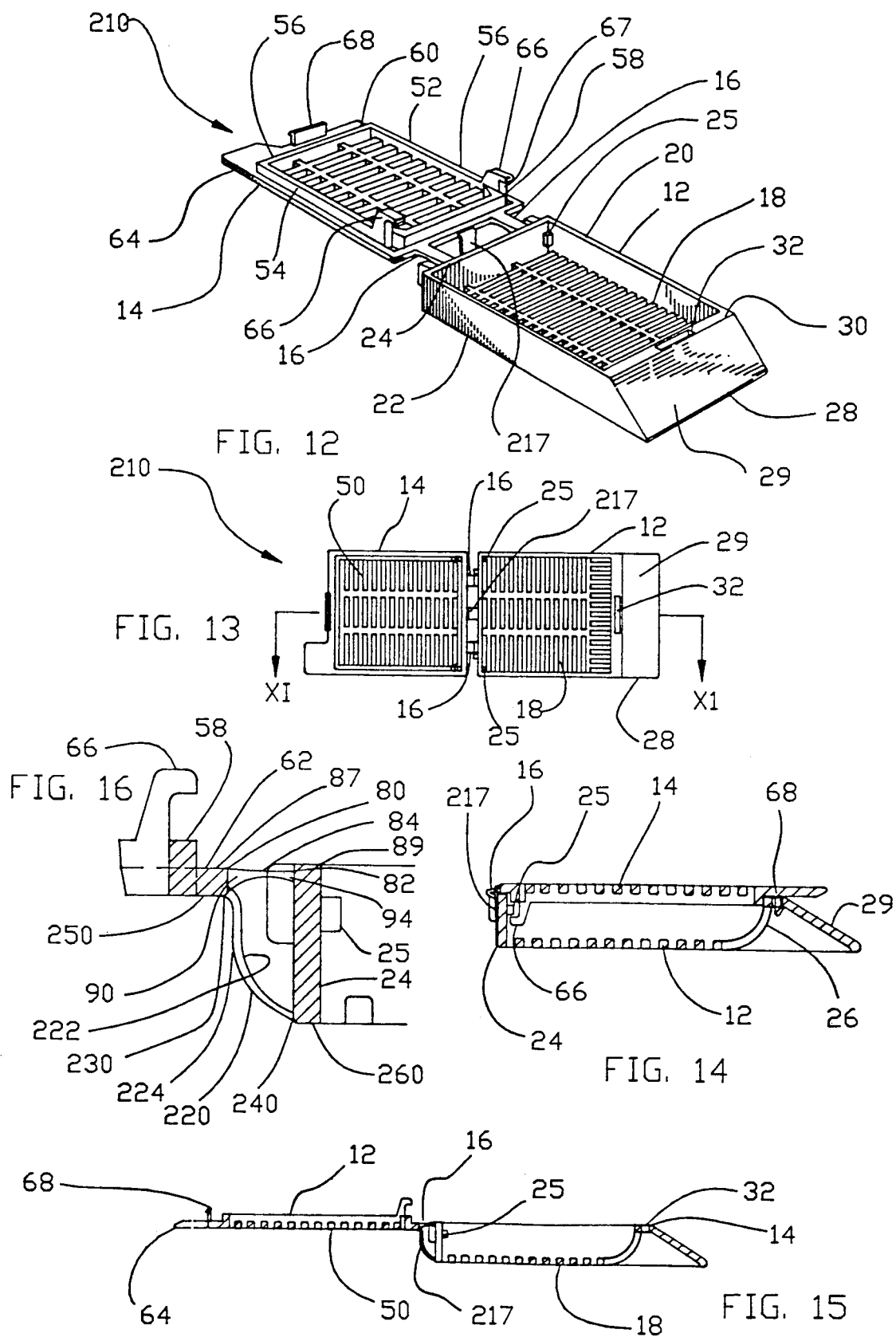

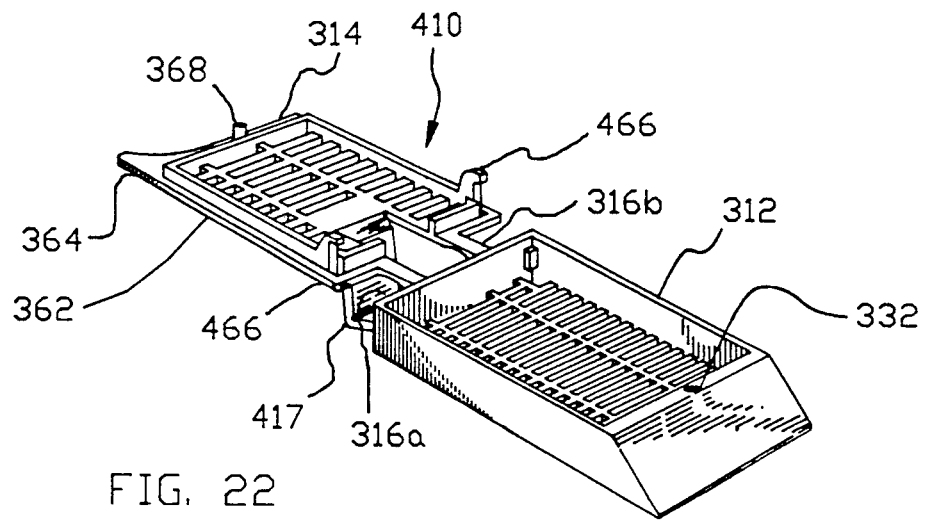
FIG. 22
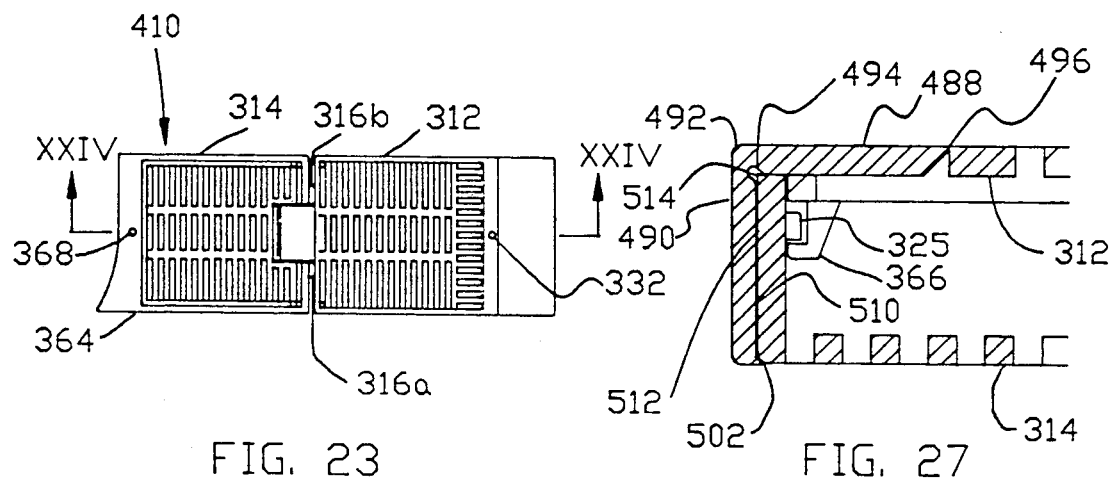
FIG. 23
FIG. 27
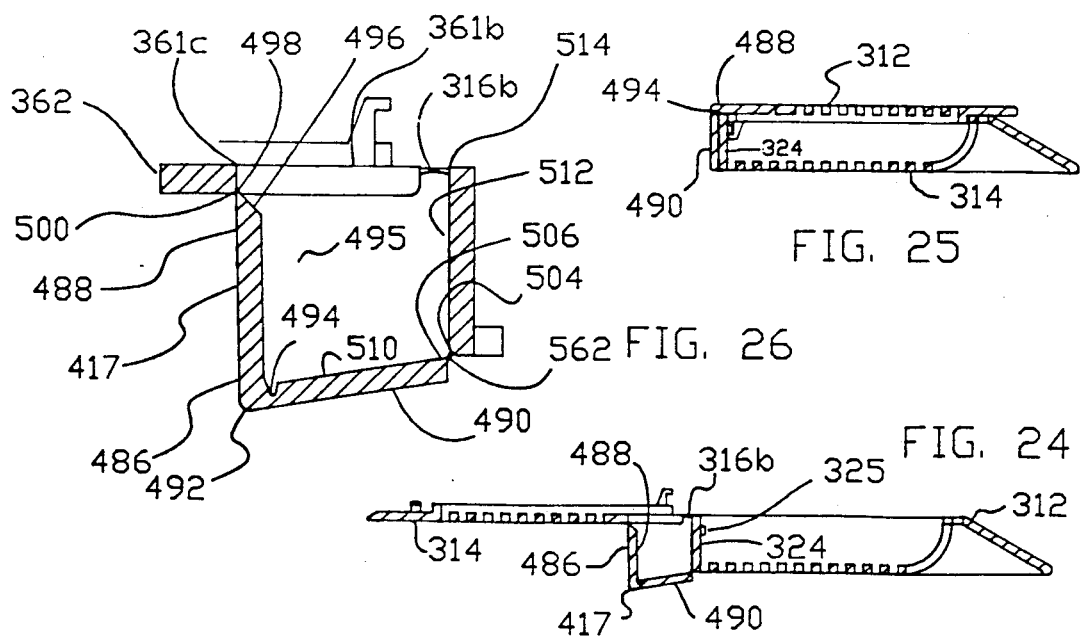
FIG. 26
FIG. 25
FIG. 24

TISSUE CASSETTE WITH A LIVING HINGE

BACKGROUND OF THE INVENTION

1. Field of the Invention

This invention relates to tissue cassettes and, more particularly, to a tissue cassette suitable for holding a biological tissue specimen while it is being treated with fluids for holding embedding tissue in a microtome for microscopic examination.

2. Description of the Prior Art

Processes for examining thin tissue slices under the microscope are well-known in the art. The tissue specimens are gathered generally through biopsies taken during exploratory surgery. They are then positioned within tissue cassettes. The tissue cassettes are then placed in a histological tissue processing chamber such as disclosed in U.S. Pat. No. 4,141,312. The chamber heats the tissue and treats the tissue with various chemicals, such as alcohols, xylene and formaldehydes. This preserves the tissue which is then embedded in paraffin in the tissue cassette. The embedded blocks are then sliced on a microtome and subsequently stained and observed by a pathologist under a microscope.

Cassettes for holding the tissue specimens are well-known in the art, for example, see U.S. Pat. Nos. 4,220,252 and 4,421,246. Both of these patents disclose tissue cassettes molded from a plastic material. Earlier tissue cassettes were manufactured with stainless steel and were expensive to make. The newer plastic tissue cassettes are much less expensive to make. Generally, patient information, such as a patient number, is directly placed on the tissue cassette for identification of the processed tissue.

Typically, the plastic tissue cassettes have a lid and an open top base member. The lid connects to the base member by an integral hinge or gate. The plastic hinges must be very thin, on the order of several thousandths of an inch, for flexibility. Hence, the hinges are frangible and usually break upon either connecting the lid to the base member or upon disconnecting the lid from the base member. This is due to both the physical properties of the plastics used, which must withstand the effects of the chemicals used in preserving the tissue, and the hinge thickness. Only a limited number of plastics can be used in the tissue processing environment. Therefore, the hinges on the plastic tissue cassettes usually do little more than keep the lids attached to the top base member prior to use.

Should a histologist want to examine a tissue specimen during the preserving processes, he or she must open the tissue cassette. Usually, by this time, the hinge is broken and the tissue cassette is in two pieces. If the tissue needs more processing, then the two pieces are connected to each other and the tissue cassette is replaced into the chamber for further processing. There is a possibility that the two-part tissue cassette will open up during this second processing, causing the tissue to fall into the chamber. Further, even if the hinge does not break immediately, the tissue cassette could open up during processing.

In practice, usually over one hundred tissue cassettes with specimens are processed at a time. These specimens come from a variety of patients who have very recently had exploratory surgery. If more than one tissue cassette opens during processing and the tissues fall into the chamber, more exploratory surgery may have to be done on the patient.

Therefore, it is an object of my invention to provide a plastic tissue cassette having a lid connected to the base member by a hinge which does not break in normal operation.

It is another object of my invention to provide a tissue cassette that remains closed during the tissue processing stage.

With various diseases, such as AIDS, lab technicians are ever wary about handling samples from patients having these diseases. Typical lab procedures for technicians processing tissues of patients having AIDS include wearing several layers of latex gloves while handling the tissue cassettes. This limits the possibility of the AIDS virus from entering the technicians, bodies through an open wound on their hands.

As mentioned above, the prior art plastic tissue cassette hinges usually break when the tissue cassette is first closed or first reopened. Typically, the broken hinges are jagged enough to cut through the technicians, two pairs of latex gloves and the technicians, hand. In fact, a common injury to the technicians prior to the above added precautions were cuts to hands from jagged edges of the broken hinges.

Therefore, it is a further object of my invention to provide a tissue cassette which decreases the possibility of a technician being injured by a broken hinge of a plastic tissue cassette.

SUMMARY OF THE INVENTION

I have invented a tissue cassette including an open topped, perforated base member adapted to receive a tissue specimen, a perforated lid member adapted to cover the base member and be secured thereto in a closed position and a snap action hinge for joining the base member to the perforated lid. The tissue cassette can further include a living hinge joining the base member to the perforated lid. Further, the invention can include two living hinges joining the base member of the perforated lid with a snap action hinge positioned between the living hinges. The tissue cassette includes means for locking the base member to the lid.

My invention also includes a tissue cassette having an open topped, perforated base member adapted to receive tissue specimens, a perforated lid member adapted to cover the base member and be secured thereto in a closed position and at least one living hinge joining the base member and the open topped member. The living hinge includes a first end attached to the lid member, a second end attached to the base member, a flat surface and a curved surface whereby the hinge thickness varies across the length of the hinge. The thinnest portion of the hinge is positioned between the first hinge end and the second hinge end. The second surface of the hinge can be concave shaped.

BRIEF DESCRIPTION OF THE DRAWINGS

FIG. 1 is a top perspective view of a first embodiment of a tissue cassette in an open position in accordance with the present invention;

FIG. 2 is a perspective view of the tissue cassette shown in FIG. 1, partially in section;

FIG. 3 is a top view of the tissue cassette shown in FIG. 1;

FIG. 4 is a section taken along lines IV—IV in FIG. 3;

FIG. 8 is a top view of the tissue cassette shown in FIG. 7;

FIG. 9 is a side view of a portion of the tissue cassette showing a hinge in detail in FIG. 7, partially in section;

FIG. 10 is a side view of the tissue cassette of FIG. 7 in a closed position, partially in section;

FIG. 11 is a section taken along lines XI—XI in FIG. 8;

FIG. 12 is a top perspective view of a third embodiment of a tissue cassette in an open position;

FIG. 13 is a top view of the tissue cassette shown in FIG. 12;

FIG. 14 is a side view of the tissue cassette of FIG. 12 in a closed position, partially in section;

FIG. 15 is a section taken along lines XV—XV in FIG. FIG. 16 is a side view of a portion of the tissue cassette showing a hinge in detail in FIG. 12, partially in section;

FIG. 22 is a top perspective view of a fifth embodiment of a tissue cassette in an open position;

FIG. 23 is a top view of the tissue cassette shown in FIG. 22;

FIG. 24 is a section taken along lines XXIV—XXIV;

FIG. 25 is a side view of the tissue cassette of FIG. 22 in a closed position, partially in section;

FIG. 26 is a side view of a portion of the tissue cassette in FIG. 22, partially in section showing a hinge in an open position; and FIG. 27 is a side view of the portion of the cassette in FIG. 26, showing the hinge in a closed position.

DESCRIPTION OF THE PREFERRED EMBODIMENTS

Figure 5:
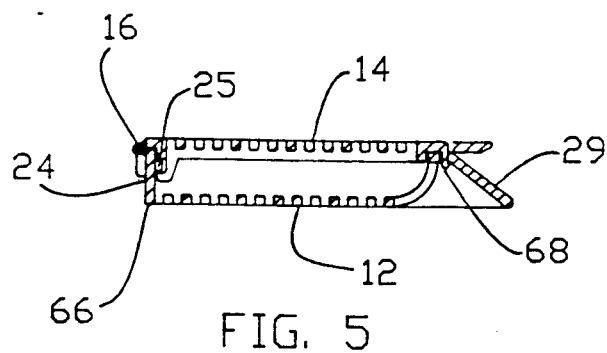
FIG. 5 is a side view of the tissue cassette of FIG. 1 in a closed position, partially in section.

FIGS. 1-6 show a first embodiment of a one-piece molded tissue cassette 10 made in accordance with the present invention. The tissue cassette 10 includes an open topped base member 12 and a lid 14 connected by two spaced apart living hinges 16. By living hinge, I mean a hinge that can be flexed many times without breaking. The base 12 and the lid 14 are substantially rectangular in shape.

The base 12 includes a flat perforated bottom 18 and four walls depending therefrom, side walls 20 and 22, back wall 24 and front wall 26. Walls 20, 22 and 24 are solid and perpendicular to the bottom 18. Wall 26 is curved and slotted, which permits better flow and drainage of the processing fluids than a solid wall and prevents air bubbles from being trapped in the tissue cassette 10. Walls 20-24 connect to one another about their respective ends. Wall 26 ends connect to respective sections of walls 20 and 22 away from their ends. Upper inner edges of walls 20-26 form a rectangle. Two rectangular shaped steps 25 extend from respective inner corners formed by walls 20 and 24, and walls 22 and 24. The steps 25 are spaced from upper edges of walls 20-24.

The base also includes an inclined wall 28 that extends forwardly of wall 26 and attaches to respective ends of side walls 20 and 22. Wall 28 includes an upper surface 29 and a lip 30 positioned between and attached to an upper edge of wall 26 and an upper edge of the upper surface 29. The upper surface 29 can contain patient information, either by the technician writing on the surface with a pen or a scribe. The lip 30 includes a centrally positioned, rectangularly shaped locking finger slot 32.

The lid 14 includes a rectangular shaped perforated section 50 surrounded by a ridge 52 that includes four walls, side walls 54 and 56, a back wall 58 and a front wall 60. A ledge 62 depends upwardly around the ridge 52. The profile of the ridge outer surface 52 is substantially geometrically similar to the profile formed by the inner top edges of walls 20-26, except the ridge profile is slightly smaller. A substantially rectangular shaped handle 64 extends outwardly from a corner portion of the ledge 62 adjacent to walls 54 and 60. Two hook-shaped guides 66, located near wall 58, depend upwardly from hinge side walls 54, 56, respectively. Each guide 66 defines an open recess 67 adapted to receive respective steps 25. A locking finger 68 depends upwardly from the ledge 62 adjacent to front wall ridge 60. The locking finger has a pointed end adapted to be received by locking finger slot 32.

Figure 6:
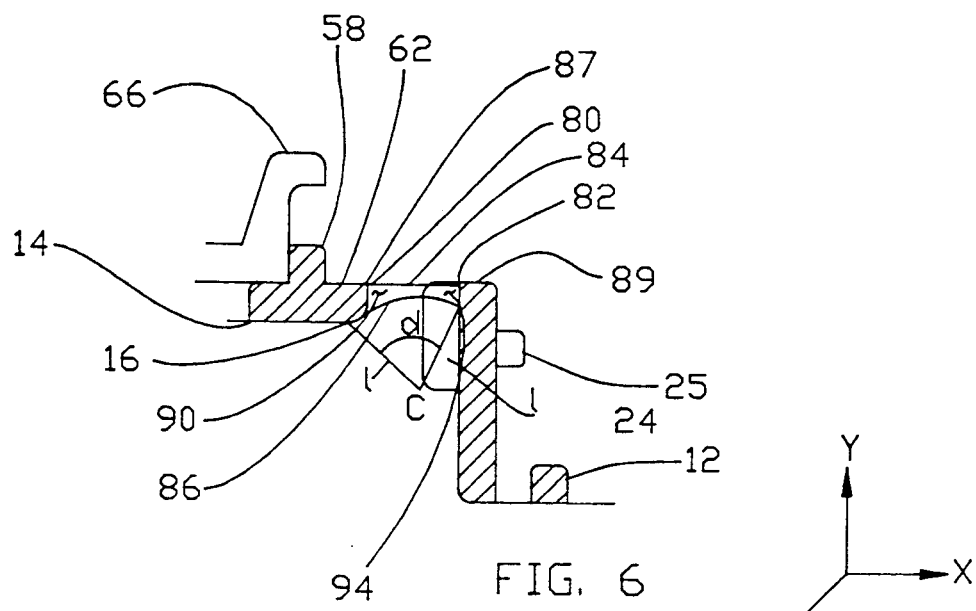
FIG. 6 is a side view of a portion of the tissue cassette showing a hinge in detail in FIG. 1, partially in section.
Figure 7:
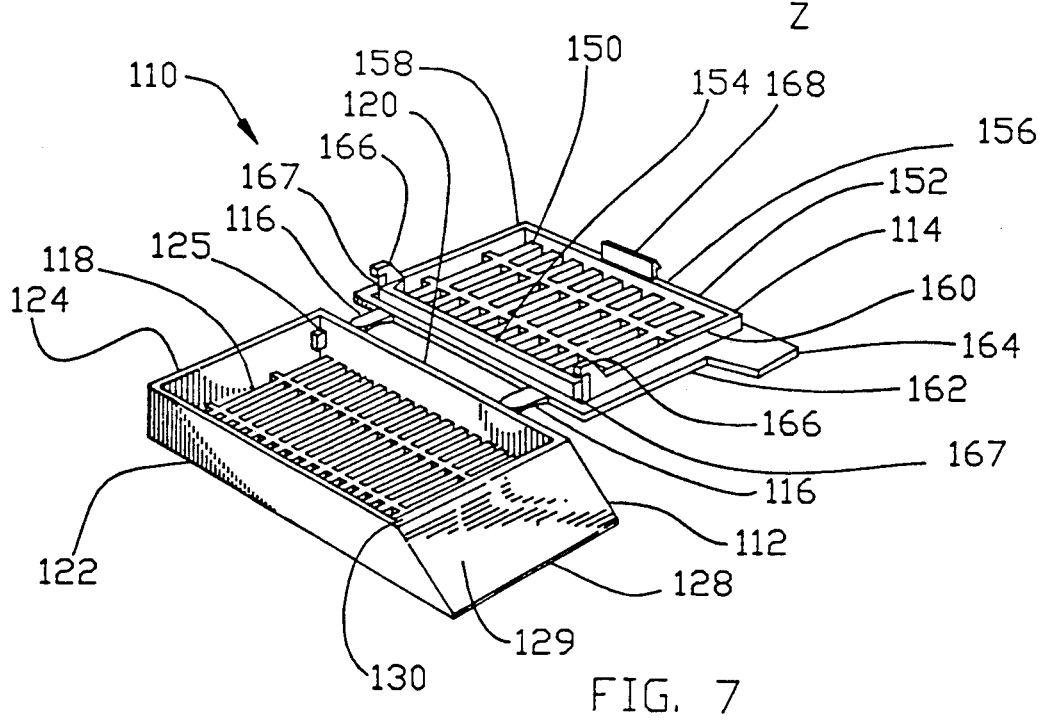
FIG. 7 is a top perspective view of a second embodiment of a tissue cassette in an open position.

The living hinges 16 are similar to each other. Accordingly, only one of the hinges 16 will be described in detail and like reference numerals will designate like parts. As shown in FIG. 6, hinge 16 includes first end 80, a second end 82, a flat first surface 84 and a curved second surface 86. Accordingly, the hinge thickness varies along its length. The hinge first end 80 attaches to a portion of the lid ledge 62 that is adjacent to lid wall 58. The hinge second end 82 attaches to a portion of an outer surface of base wall 24.

The hinge first end 80 and second end 82 have equal thicknesses. Specifically, the thickness of the hinge 16 at end 80 is the same as the lid ledge thickness. The thickness of hinge end 82 is determined by the second surface 86, which is concave. The concave surface is defined by a line having a length r, which is rotated a radial distance about a center point c. The thinnest portion of the hinge 16 is preferably positioned at the midpoint between the two ends 80 and 82. For example, in an actual prototype the radial distance was 0.100", the hinge length was 0.099", and the thinnest portion of the hinge was 0.015".

I have found that the living hinge works best if the hinge first surface 82 and an upper surface 87 of the lid ledge 62 are contained within the same plane and the first surface 84 is offset several thousandths of an inch (for example, 0.003") from an upper surface 89 of base wall 24.

The hinge also includes parallel side surfaces 90, 92 that extend from first end 80 to an intermediate section 94. The hinge width is constant over this portion. Inclined surfaces 96, 98 extend from intermediate section 94 to second end 82, whereby the hinge width decreases from the intermediate section 94 to second end 82. An actual prototype had inclined surfaces 96, 98 positioned at an angle of 49° from base wall 24. Preferably, the angle should be between 40°–60°.

As stated above, only a limited number of plastics can be used for the tissue cassettes. In most applications, the tissue cassettes can be made from Celcon ®️ acetic copolymers, manufactured by Celanese, although other plastics may be used, for example, Hostalen ®️ GUR, manufactured by Hoerst Celanese, or polyethylenes, such as Hostaform ®️, manufactured by Hoerst Celanese.

In operation, the sample is placed within the tissue cassette 10 and then the lid is rotated about the z axis so that the guides 66 receive the steps 25 in the respective guide recesses 67, and the locking finger slot 32 received locking finger 68. It is contemplated that any type of locking arrangement can be used, such as a pin and pin receiving hole arrangement, discussed below. In the closed position, the outer surface of the ridge 52 is slideably received between inner surface walls 20–26. The patient information can then be written on the inclined surface 29 by an appropriate marking pen or scribe. The tissue cassette is then placed in a processing chamber and the specimen is processed as discussed above. The perforated sections of the tissue cassette permit the processing fluids to contact the specimen. The technician can open the tissue cassette 10 by the handle 64 and close the tissue cassette many times during processing without the fear of the hinge 16 breaking, as is the case with the prior art.

Once the tissue is properly processed, the lid 14 can be removed from the body 12 by twisting it about the x axis so that the tissue cassette interior can be filled with molten paraffin to embed the tissue therein. It is important that (1) the offset of the hinge 16 with second end 82 and upper surface 89 of base wall 24 and (2) the hinge inclined surfaces 96, 98 be present so that hinges 16 will break cleanly away at their second ends 82. This reduces the risk of injury to a technician because of jagged edges that are present in broken hinges of tissue cassettes.

A second embodiment of a one-piece, molded tissue cassette 110 is shown in FIGS. 7–11. The tissue cassette 110 is similar to the tissue cassette 10 except for the position of the hinges, as will be explained below. The tissue cassette 110 includes an open-topped base member 112 and a lid 114 connected by two spaced apart living hinges 116.

The base 112 includes a flat perforated bottom 118 and four walls depending therefrom, side walls 120 and 122, back wall 124 and front wall 126. Walls 120–126 are similar to walls 20–26, except that wall 122 has a centrally positioned locking finger recess 127. Two rectangular shaped steps 125 extend from respective inner corners formed by walls 120 and 124, and walls 120 and 126. The steps 125 are spaced from upper edges of walls 120, 124 and 126. An inclined wall 128 extends forwardly of wall 126 and attaches to respective ends of side walls 120 and 122. Wall 128 includes an inclined upper surface 129 and a lip 130 positioned between and attached to an upper edge of wall 126 and an upper edge of the upper surface 129.

The lid 114 includes a rectangular shaped perforated section 150 surrounded by a ridge 152 that includes four walls, side walls 154 and 156, a back wall 158 and a front wall 160. A ledge 162 depends upwardly around the ridge 152. A substantially rectangular shaped handle 164 extends outwardly from a corner portion of the ledge 162 adjacent to walls 156 and 160. Two hook-shaped guides 166 located near wall 154 depend upwardly from ridge walls 158, 160, respectively. Each guide 166 defines a recess 167 adapted to receive respective steps 125. A locking finger 168 depends upwardly from the ledge 162 adjacent to wall 156. The locking finger 168 has a pointed end adapted to be received by locking finger recess 127.

The living hinges 116 are similar to hinges 16 and will not be explained in detail. Hinge 116 includes first end 180, a second end 182, a flat first surface 184 and a curved second surface 186. The hinge first end 180 attaches to a portion of the lid ledge 162 that is adjacent to lid wall 154. The hinge second end 182 attaches to a portion of base wall 120.

Cassette 110 operates similarly to tissue cassette 10, except the lid 114 is rotated about the x axis to close tissue cassette 110 and the base 112 is rotated about the z axis to remove the lid 114 from the base 112.

A third embodiment of a one-piece molded tissue cassette 210 is shown in FIGS. 12–16. The tissue cassette 210 is similar to the tissue cassette 10 except for the addition of a snap action hinge 217. Therefore, like reference numerals of tissue cassette 10 will be used for like parts of tissue cassette 210.

The snap action hinge or snap hinge 217 is equally spaced from and centrally positioned between hinges 16. As shown in FIG. 16, the snap action hinge 217 includes a curved or sinusoidal shaped body 220 having an upper surface 222 and a lower surface 224, a first end 230 and a second end 240. Snap hinge first end 230 attaches to a portion of the lid ledge 62 that is adjacent to the lid wall 58. Snap hinge second end 240 adjacent to the lid wall 58. Snap hinge second end 240 attaches to a lower portion of base wall 24. The snap hinge lower surface 224 located at first end 230 is flush with a lower surface 250 of lid ledge 62. Likewise, the snap hinge lower surface 224 located at second end 240 is flush with a lower surface 260 of base wall 24. Preferably, the hinge thickness is less than the thickness of the lid ledge 62, and should be on the order of several thousandths of an inch.

The snap action hinge can maintain the tissue cassette in two positions-in the open position, as shown in FIG. 12 or in the closed position, as shown in FIG. 14. The snap action hinge is unstable when positioned in the intermediate positions between the opened and closed positions and applies stresses to the lid so as either to force the lid in the open or closed position. Accordingly, the tissue cassette will remain closed during processing even if the technician forges to snap the lid closed prior to processing or the locking finger works its way loose from the locking finger slot during processing. Other than this, tissue cassette 210 operates in the same manner as tissue cassette 10 so that when the lid is removed from the body, the hinges 16 and snap action hinge 217 break away flush with the outer surface of base wall 24.

A fourth embodiment of a one-piece molded tissue cassette 310 is shown in FIGS. 17–21. Like tissue cassette 210, tissue cassette 310 includes both living hinges and a snap action hinge. The tissue cassette 310 includes an open topped base member 312 and a lid 314 connected by two spaced apart living hinges 316a, 316b and a snap action hinge 317.

The base 312 includes a flat perforated bottom 318 and four walls depending therefrom, side walls 320 and 322, back wall 324 and front wall 326. Walls 320–326 are similar to walls 20–26. Two rectangular shaped steps 325 extend from respective inner corners formed by walls 320 and 324, and walls 322 and 324. Steps 325 are similar to steps 25. An inclined wall 328 extends forwardly of wall 326 and attaches to respective ends of side walls 320 and 322. Wall 328 includes an inclined upper surface 329 and a lip 330 positioned between and attached to an upper edge of wall 326 and an upper edge of the upper surface 329. The lip 330 includes a centrally positioned circular shaped locking pin hole 332.

The lid 314 includes a rectangular shaped perforated section 350 surrounded by a ridge 352 that includes five walls, side walls 354 and 356, a back wall 358 and front walls 360a and 360b. A U-shaped recess 361 extends from a forward portion of the lid toward back wall 358. Recess 361 is defined by two parallel leg edges 361a, 361b and a base edge 361c. Walls 360a and 360b extend from edges 361a and 361b, respectively.

A ledge 362 depends outwardly around the ridge 352. A handle 364 having a rounded tip extends outwardly from a corner portion of the ledge 362 adjacent to walls 354 and 358. Two guides 366a, 366b, located near walls 360a, 360b, depend upwardly from ridge side walls 354, 356, respectively. Guides 366a, 366b differ from previously described guides 266, 166 and 66 in that they are substantially box-shaped and have two open adjacent sides with a recess 367 defined therein. The guide recess 367 receives steps 325. A cylindrical locking pin 368 depends upwardly from the ledge 362 adjacent to wall 360. The locking pin 368 is adapted to be received by hole 332 and be frictionally held in place.

The living hinges 316a and 316b are similar to hinges 16 and will not be discussed in detail. Each hinge 316a, 316b includes first end 380, a second end 382, a flat first surface 384 and a curved second surface 386. The hinge first end 380 attaches to a portion of the lid ledge 362 that is adjacent to lid wall 360a or 360b. The hinge second end 382 attaches to a portion of base wall 324.

Figures 20, 21:
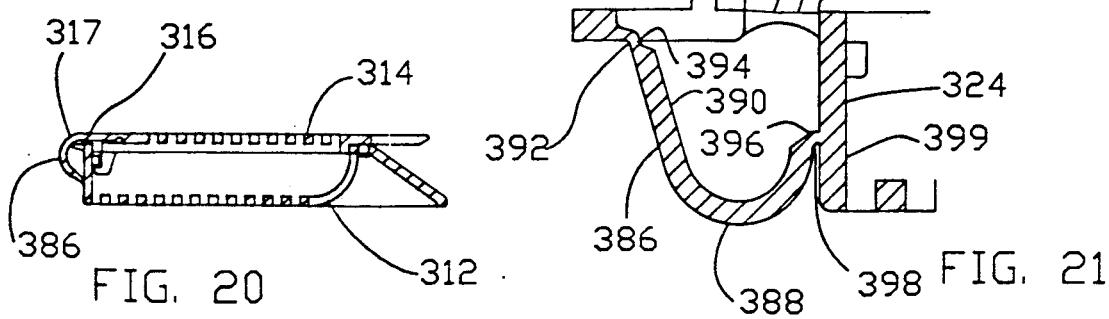
FIG. 20 is a side view of the tissue cassette of FIG. 17 in a closed position, partially in section.
FIG. 21 is a side view of a portion of the tissue cassette showing a hinge in detail in FIG. 17, partially in section.

The snap action hinge 317 is positioned between hinges 16 and has a width approximately equal to the length of base edge 361c defining the U-shaped recess 361. As shown in FIG. 21, the snap action hinge 317 includes a J-shaped body 386 having an arcuate first section 388 attached to a straight second section 390. The J-shaped body thickness is approximately equal to the thickness of the ledge 362. A lid connecting section 392 attaches to an end 394 of first section 390 and the recess edge 361c. The lid connecting section 392 is thinner than the J-shaped body 386. Bottom surfaces of the lid connecting section 392, ledge 362 and straight second section 390 are flush with each other at their respective points of attachment. A base connecting section 396 attaches an end 398 of arcuate first section 388 to an intermediate section 399 of base wall 324. Base connecting section 396 has approximately the same thickness as the lid connecting section 392.

Figure 17:
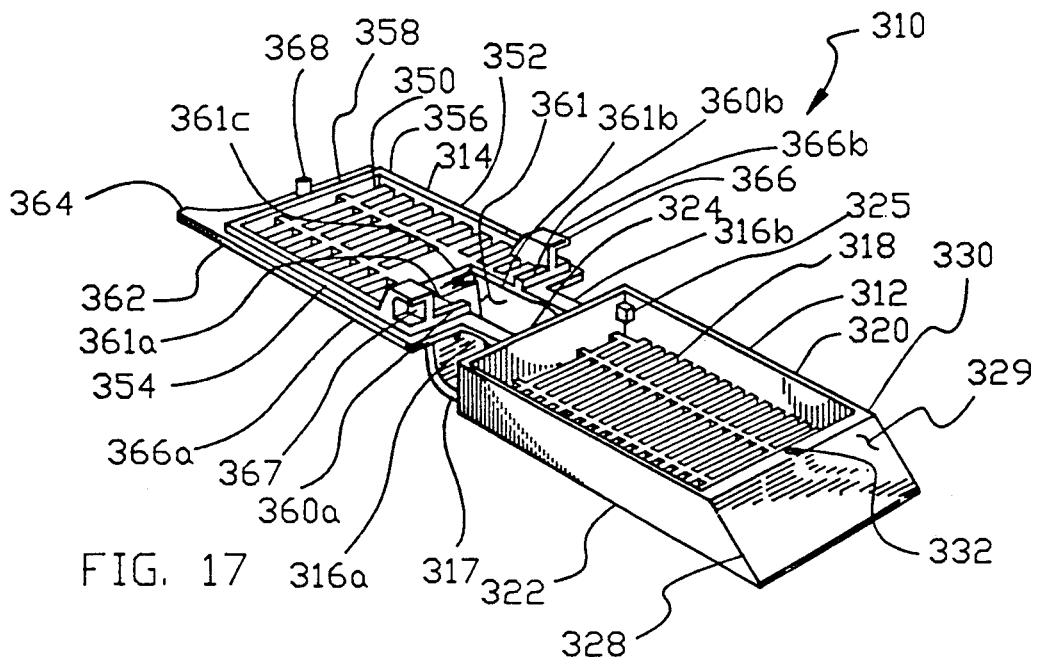
FIG. 17 is a top perspective view of a fourth embodiment of a tissue cassette in an open position.
Figure 18:
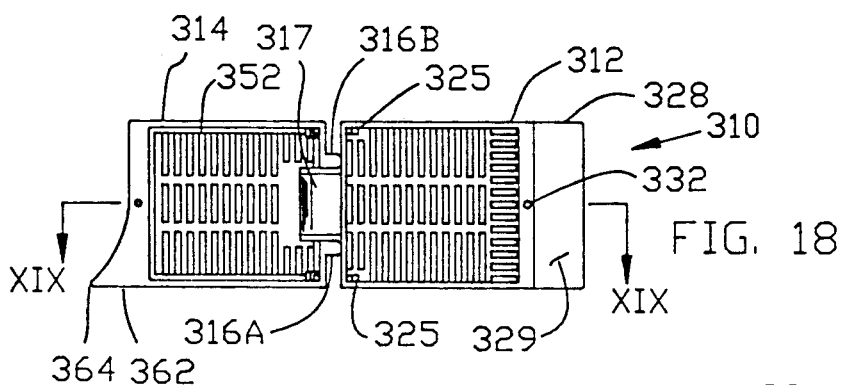
FIG. 18 is a top view of the tissue cassette shown in FIG. 17.
Figure 19:
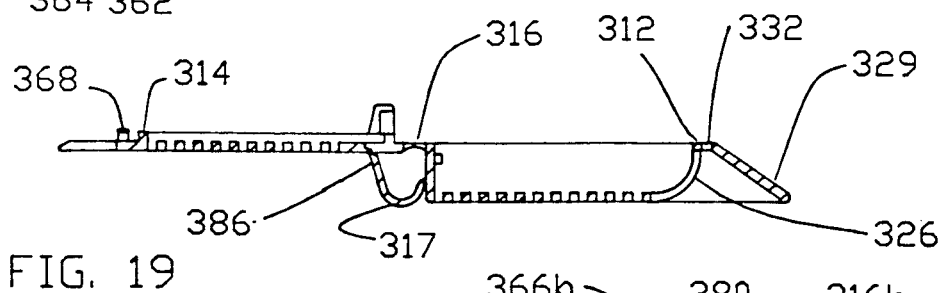
FIG. 19 is a section taken along lines XIX—XIX in FIG. 18.

In operation tissue cassette 310 operates similarly to tissue cassette 210. The snap action hinge can maintain the tissue cassette 310 in two positions-in the open position, as shown in FIG. 17, or in the closed position, as shown in FIG. 20. In the intermediate positions, the snap action hinge is unstable and applies stresses to the lid so as either to force the lid in the opened position or closed position. The actual bending of the snap action hinge 317 occurs along the connecting sections 392 and 396. In the closed position, the bottom surfaces of the lid connecting section 392, the ledge 362 and the straight second section 390 are contained within the same plane.

A fifth embodiment of a one-piece molded tissue cassette 410 is shown in FIGS. 22-27. The tissue cassette 410 is similar to the tissue cassette 310 except for two differences. First, the snap action hinge 417 replaces snap action hinge 317. Second, hook-shaped guides 466, similar to guides 66, replace guides 366. Therefore, like reference numerals of tissue cassette 310 will be used for like parts of tissue cassette 410.

The snap action hinge 417 is positioned between hinges 316a and 316b, and has a width approximately equal to the length of edge 361c of the lid 314. As shown in FIG. 26, the snap action hinge 417 includes an L-shaped body 486 having a straight first leg 488 and a straight second leg 490. Respective first ends of legs 488 and 490 are joined together by a leg connecting section 492. Leg connecting section 492 includes a V-shaped notch 494 positioned adjacent to leg 490. The notch 494 faces the interior portion 495 of the L formed by the body 486.

A substantially triangular cross sectional shaped lid connecting section 496 attaches to a second end of leg 488. A top section 498 of connecting section 496 attaches to a lower corner 500 of edge 361c. A rectangular cross sectional shaped base connecting section 502 attaches to bottom 504 of base wall 324 and a second end inner edge 506 of the second end of leg 490.

Legs 488 and 490 are angularly spaced apart less than 90 degrees and are approximately the same thickness as the base wall 324 and ledge 362. The thickness of the top section 498 of connecting section 496 and the thickness of connecting section 502 are substantially less than the thickness of legs 488 and 490. The thickness of connecting section 492 at the base of the V-shaped notch 494 is approximately one-half the thickness of legs 488 and 490.

The snap action hinge 417 can maintain the tissue cassette 410 in either the opened position or the closed position. In the opened position, as shown in FIG. 26, leg 488 depends from lid 314 and leg 490 depends from base wall 324. In the closed position, as shown in FIG. 27, inner surface 510 of leg 490 abuts against a portion of the outer surface 512 of base wall 324; the V-shaped notch receives a portion of the upper corner 514 of base wall 324; one plane contains upper surfaces of leg 488, connecting section 496 and ledge 362; and legs 488 and 490 are angularly spaced apart by 90 degrees from each other. In the intermediate positions, the snap action hinge 417 is unstable and applies stresses to the lid so as either to force the lid in the opened or closed position. The actual bending of the snap action hinge 417 occurs along the connecting sections 492, 496 and 502.

The above described snap action hinges must be living hinges. Also, the various features of the above-described tissue cassettes can be interchanged with each other. Further, corners of the lids and bases preferably should have radii to prevent injury to the technicians.

Having described the presently preferred embodiments of my invention, it is to be understood that it may be otherwise embodied within the scope of the appended claims.

I claim:

1. A tissue cassette comprising:
   a) an open-topped, perforated base member adapted to receive a tissue specimen;
   b) a perforated lid member adapted to cover the base member and be secured thereto in a closed position;
   c) a snap action hinge joining the base member to the perforated lid; and d) a living hinge joining said base member to said perforated lid, said living hinge having a first end attached to said lid member, a second end attached to said base member, a flat first surface and a curved second surface whereby said hinge having a thickness that varies across a length of said hinge, said first surface of said hinge being offset from an upper surface of said base member wherein said offset permits a breaking away of said living hinge and said snap action hinge flush with a surface of said base member.

2. The tissue cassette of claim 1 further comprising:
a) two living hinges joining said base member and the perforated lid wherein said snap action hinge is positioned between said living hinges.

3. The tissue cassette of claim 1 wherein said snap action hinge comprises:
a J-shaped body having an arcuate section attached to a straight section, an end of said straight section attached to said lid and an end of said arcuate section attached to said base.

4. The tissue cassette of claim 3 further comprising a lid connecting section attached to said end of said J-shaped body straight section and said lid, and a base connecting section attached to said end of said arcuate section of J-shaped body and said lid, said lid connecting section and said base connecting section are thinner than said J-shaped body.

5. The tissue cassette of claim 3 wherein said lid includes a recess extending from a forward portion of said lid and defined by at least one edge, said end of said straight section of said J-shaped body attached to said edge.

6. The tissue cassette of claim 1 further comprising means for locking said base member to said lid.

7. The tissue cassette of claim 1 wherein said base is substantially a rectangularly shaped structure with a perforated bottom having at side edges and a back wall and a pair of opposed side walls extending upwardly from and connected to the outside edges of the bottom, with a front wall extending between and connected to said side walls, upper inner edges of said front wall, back wall and said side walls defining a rectangle, said lid having a lip with rectangular shape which is geometrically similar to and smaller than said upper inner edge rectangle defined by said base.

8. The tissue cassette of claim 1 wherein said front wall is curved and perforated, said wall is connected to said bottom, said base further including a sloped wall positioned forward of said front wall and attached to said side walls.

9. The tissue cassette of claim 1 wherein said curved second surface is concave shaped and said hinge having a thinnest portion positioned between said hinge ends.

10. The tissue cassette of claim 1 wherein said hinge is thinnest at a mid point between said first end and said second end.

11. A tissue cassette comprising:
a) an open-topped, perforated base member adapted to receive a tissue specimen;
b) a perforated lid member adapted to cover the base member and be secured thereto in a closed position; and
c) at least one living hinge joining said lid member to said open-topped base member, said living hinge having a first end attached to said lid member and a second end attached to said base member, and a flat first surface and a curved second surface, whereby said hinge having a thickness that varies across a length of the hinge, said hinge having a thinnest portion positioned between said hinge ends, said first surface of said hinge being offset from an upper surface of said base.

12. The tissue cassette of claim 11 wherein said second surface of said hinge is concave shaped.

13. The tissue cassette of claim 11 wherein said living hinge has a constant width from said first end to an intermediate section and a decreasing width from said intermediate section to said second end.

14. A tissue cassette comprising:
a) an open-topped, perforated base member adapted to receive a tissue specimen;
b) a perforated lid member adapted to cover the base member and be secured thereto in a closed position, said lid member having a ledge; and
c) a snap action hinge joining the base member to the perforated lid member, wherein said snap action hinge includes a curved sinusoidal shaped body having a first end, a second end and a lower surface, said first end attached to said lid member ledge and said second end attached to said base, and said lower surface of said first end of said snap action hinge body is flush with a lower surface of said ledge and said lower surface of said second end of said snap action hinge is flush with a lower surface of said base.

15. A tissue cassette comprising:
a) an open-topped, perforated base member adapted to receive a tissue specimen;
b) a perforated lid member adapted to cover the base member and be secured thereto in a closed position; and
c) a snap action hinge joining the base member to the perforated lid member, said snap action hinge comprising an L-shaped body having a first leg, a second leg and a leg connecting section having a V-shaped notch, said first leg joined together to said second leg by said leg connecting section; a lid connecting section having a triangular-shaped cross-section; and a base connecting section having a rectangular-shaped cross-section, said first leg attached to said lid by said lid connecting section and said second leg attached to said base by said base connecting section, wherein said first leg and said second leg arm thicker than a top section of said lid connecting section and said base connecting section.

16. A tissue cassette comprising:
a) an open-topped, perforated base member adapted to receive a tissue specimen;
b) a perforated lid member adapted to cover the base member and be secured thereto in a closed position; and
c) at least one living hinge joining said lid member to said open-topped base member, said living hinge having a first end attached to said lid member and a second end attached to said base member, and a flat first surface and a curved concave-shaped second surface, wherein said hinge first surface being offset from an upper surface of said base member and said hinge having a thickness that varies across a length of said hinge, said hinge having a thinnest portion positioned between said hinge ends, and said hinge having a constant width from said first end to an intermediate section and a decreasing width from said intermediate section to said second end.

17. A tissue cassette comprising:
a) an open-topped, perforated base member adapted to receive a tissue specimen;
b) a perforated lid member adapted to cover the base member and be secured thereto in a closed position; and
c) at least one living hinge joining said lid member to said open-topped base member, said living hinge having a first end attached to said lid member and a second end attached to said base member, and said living hinge having a first flat upper surface and a second lower surface positioned below said first upper surface, at least a portion of said second surface being curved, said first upper surface of said hinge being offset from an upper surface of said base member.

18. The tissue cassette of claim 17 wherein said living hinge has a constant width from said first end to an intermediate section and a decreasing width from said intermediate section to said second end.

19. The tissue cassette of claim 17 wherein said first upper surface of said hinge is positioned below said second upper surface of said base member.

* * * * *

UNITED STATES PATENT AND TRADEMARK OFFICE
CERTIFICATE OF CORRECTION

PATENT NO. : 5,127,537
DATED : July 7, 1992
INVENTOR(S) : Donald R. Graham

It is certified that error appears in the above-identified patent and that said Letters Patent is hereby corrected as shown below:

Column 2 Line 16 "technicians," should read --technicians'--.

Column 2 Lines 21-22 "technicians," should read --technicians'--.

Column 2 Line 22 "technicians," should read --technicians'--.

Column 3 Line 22 after "FIG." (first occurrence) insert --13;-- and begin new paragraph with "FIG. 16".

Column 5 Lines 14-15 "received" should read --receives--.

Column 6 Lines 32-33 delete "Snap hinge second end 240 adjacent to the lid wall 58.".

Claim 7 Line 38 Column 9 "at side" should read --outside--.

Claim 15 Line 48 Column 10 "arm" should read --are--.

Signed and Sealed this

Twenty-fourth Day of August, 1993

Attest:

Attesting Officer

BRUCE LEHMAN

Commissioner of Patents and Trademarks